(12) United States Patent
Smith

(10) Patent No.: US 6,958,159 B2
(45) Date of Patent: Oct. 25, 2005

(54) PHARMACEUTICAL GEL COMPOSITION

(75) Inventor: Robert Alan Smith, Liverpool (AU)

(73) Assignee: Chiltern Pharmaceuticals, Pty Ltd., Syndey (AU)

( * ) Notice: Subject to any disclaimer, the term of this patent is extended or adjusted under 35 U.S.C. 154(b) by 0 days.

(21) Appl. No.: 10/240,053

(22) PCT Filed: Mar. 26, 2001

(86) PCT No.: PCT/AU01/00331

§ 371 (c)(1),
(2), (4) Date: Jan. 22, 2003

(87) PCT Pub. No.: WO01/72310

PCT Pub. Date: Oct. 4, 2001

(65) Prior Publication Data

US 2003/0147942 A1 Aug. 7, 2003

(30) Foreign Application Priority Data

Mar. 27, 2000 (AU) .......................................... PQ-6476

(51) Int. Cl.[7] ...................... A61K 31/19; A61K 31/717; A61K 33/06; A61K 9/06; A61P 17/02
(52) U.S. Cl. ...................... 424/445; 424/443; 424/446; 424/447; 424/682; 424/684; 424/685; 424/686; 424/688; 424/689; 424/690; 424/691; 424/698; 424/DIG. 13; 514/57; 514/171; 514/553; 514/557; 514/574; 514/680; 514/738; 514/781; 514/829; 514/831; 514/886; 514/887; 514/925; 514/928; 514/944; 514/966
(58) Field of Search ...................... 424/443, 445–447, 424/682, 684–686, 688–691, 698, DIG. 13; 514/57, 171, 553, 557, 574, 680, 738, 781, 829–831, 886, 887, 925, 928, 944, 966

(56) References Cited

U.S. PATENT DOCUMENTS 4,604,384 A    8/1986  Smith et al.
4,840,798 A  * 6/1989  Skaliotis .................... 424/488
5,120,544 A  * 6/1992  Henley ....................... 424/443
6,207,184 B1 * 3/2001  Ikeda et al. ................ 424/448

FOREIGN PATENT DOCUMENTS

AU    558482    2/1984
CN   1050502    4/1991

OTHER PUBLICATIONS

Derwent Abstract, accession No. 1994–206337, abstracting JP 6–145053 (May 1994).*
Burch, R.M.et al., "Sucralfate Induces Proliferation of Dermal Fibroblasts and Keratinocytes in Culture and Granulation Tissue Formation in Full–tickness Skin Wounds", *Agents and Actions*, vol. 34, 1/2, pp. 229–231; 1991.
Gabbar, F. et al., "Comparative Study on Gingival Retraction Using Mechanochemical procedure and Pulsed ND=YAG Laser Irradiation.", *Egyptian Dental Journal*, vol. 41, pp. 1001–1006; 1995.
Madison, J.B. et al., "Effects of a Proprietary Topical Medication on Wound Healing and Collagen Deposition in Horses.", *Am.J. Vet. Res.*, vol. 52, No. 7, pp. 1128–1131; 1991.
Maiche, A. et al., "Skin Protection by Sucralfate Cream During Electron Beam Therapy", *Acta Oncologica*, vol. 33, No. 2, pp. 201–203; 1994.
The Merck Index: *An Encyclopedia of Chemical, Drugs, and Biologicals*, 12th Edition, Merck & Co., Inc., 1996.
Rees, W.D.W., "Mechanisms of Gastroduodenal Protection by Sucralfate", *The American Journal of Medicine*, vol. 91, (suppl. 2A), pp. 58S–63S; 1991.
Remington: *The Science and Practice of Pharmacy*, 19th Edition, Mack Publsh. Co., pp. 871, 872, 887, 1263, 1264, 1397, 1402, 1403. 1995.

* cited by examiner

*Primary Examiner*—John Pak
(74) *Attorney, Agent, or Firm*—Fish & Richardson P.C.

(57) ABSTRACT

The present invention relates to an improved pharmaceutical composition useful for the topical treatment of burns, cuts, wounds, abrasions and the like, and to methods of treatment of injured body surfaces such as skin.

6 Claims, 6 Drawing Sheets

PHARMACEUTICAL GEL COMPOSITION

Pursuant to 35 USC §371, this application claims priority to PCT/AU01/00331, filed on Mar. 26, 2001, the contents of which are incorporated herein by reference.

TECHNICAL FIELD

The present invention relates to an improved pharmaceutical compositions which may be used for the topical treatment of burns, cuts, wounds, abrasions and the like and to a method of treatment of burned or otherwise injured skin.

BACKGROUND ART

In the treatment of burns it is difficult to avoid the formation of hypertrophic scarring with consequent contractures and detrimental effect on muscle movement recovery. Combating infection is also difficult, particularly when the site of infection is shielded for example by burn eschar.

In the treatment of burns it is usual to combat infection by use of compositions comprising one or more active ingredient in an inert pharmaceutical carrier.

The active ingredient is typically an antibiotic such as neomycin sulphate or micronized silver sulphadiazine; an anti-bacterial agent such as cetrimide chlorhexidine gluconate or dibromopropamide isethionate, and for minor burns a local anaesthetic such as lignocaine or a mixture of such ingredients.

The inert carrier or vehicle is commonly selected having regard to the solubility of the active constituent to be carried and for those mentioned above is usually a paraffin base ointment or an oil-in-water emulsion cream. For minor injuries, lanolin and petroleum bases have been used. Aqueous gels, such as those formed with hydroxy methyl cellulose or polyacrylic acid have not hitherto found favour for treatment of injuries where there is skin lesion or for burns.

In pharmaceutical compositions of the type discussed each of the active ingredients performs its expected function. In addition to acting as a vehicle for the active ingredient, the inert carrier in many such preparations acts as a barrier to moisture transpiration.

As a general rule neither the active ingredient nor the vehicle plays any therapeutic part in skin regrowth. Possible exceptions are the use in such compositions of paraffin which has been said to promote the rapid formation of granulation tissue and the inclusion in some compositions of allantoin which has been said to aid tissue regeneration.

Australian patent No. 558482 describes a pharmaceutical gel composition for topical treatment of wounds which consists of propylene glycol and hydroxyethyl cellulose. This composition is effective in wound treatment as well as a barrier against bacterial contamination and mechanical abrasion.

However, there is still a need for improved compositions for treatment of wounds, cuts, abrasions and the like.

The object of the present invention is to provide an improved composition for topical treatment of wounds and the like, or at least provide a useful alternative.

SUMMARY OF THE INVENTION

It has been unexpectedly found that the combination of an aluminum containing compound with a glycol and a cellulose derivative gives rise to a formulation with improved properties when compared to composition including combination of only a glycol and a cellulose derivative such as described in AU558482 (incorporated in its entirety herein by reference) and referred to herein as SOLUGEL.

Thus, according to a first aspect the present invention provides a topical composition for treatment of wounds, including a glycol, a cellulose derivative and an aluminum compound.

Preferably the topical composition includes, per 100 parts by weight of composition:
from 15 to 30 parts by weight of a glycol.
from 1 to 4 parts by weight of a cellulose derivative,
from 0.5 to 10 parts by weight of an aluminum compound, and
the balance water.

The composition may optionally also include sodium chloride, preferably in the amount of up to 2 parts by weight of the composition.

Preferably the aluminum compound is aluminum acetate however it will be clear to those skilled in the art that other aluminum compounds, particularly salts which are water soluble, could also be used in the preparation of the composition.

For preference the glycol is propylene glycol, and comprises from 20–30% w/v of the composition. Even more preferred is the content of 22 to 28 parts of glycol by weight of the composition.

Desirably the cellulose derivative is hydroxy ethyl cellulose and is used in an amount of less than 4% w/v of the composition. However, it will be understood that where a preparation of higher viscosity is desirable, such as for example for use in the oral cavity or in the anal canal, a higher content of cellulose derivative or similar agent can be used. For example a content of 10 to 20 parts by weight a cellulose derivative could be used. The final content used in the formulation can be easily determined by those skilled in the art of formulating medicinal preparations, by reference to standard texts such as for example "Remington: The Science and Practice of Pharmacy" 1995 (Mack Publishing Company, Easton Pa.), incorporated herein by reference.

A portion of the water used in the exemplified formulation may be replaced with one or more other pharmaceutically acceptable carriers or excipients, such as those described in "Remington: The Science and Practice of Pharmacy" 1995 (Mack Publishing Company, Easton Pa.), incorporated herein by reference.

The composition is preferably an aqueous gel composition. Further, the composition may be sterilised by known means but preferably it is sterilised by heat such as for example by autoclaving.

According to a second aspect the invention provides a wound dressing including a composition according to the first aspect.

Preferably the compositions are applied or impregnated into the wound dressing such as an adhesive dressing, a bandage or the like. Suitable dressings for application in the oral cavity or the anal canal may also be used.

According to a third aspect the invention provides a method for the topical treatment of wounds including the step of topical application thereto of a composition according to the first aspect or a wound dressing according to the second aspect.

For preference the wounds to be treated are localised on the skin but it will be understood that wounds present for example in the oral cavity or the anal canal can also be treated with the compositions of the present invention. Compositions for such use may be desirably modified by the addition of a higher content of a viscosity agent such as a cellulose derivative.

Preferably the wound to be treated is a burn, a cut or an abrasion and even more preferably it is a post-operative surgical wound.

According to a fourth aspect the invention provides the use of a composition according to the first aspect for the manufacture of a medicament for the topical treatment of wounds.

When a composition according to the invention is applied to a burned, cut, wounded or abraded skin surface an adherent flexible set jelly is formed, the depth and strength of which can be controlled by the number of coats applied.

Once formed the jelly acts as an effective barrier to contamination and mechanical interference.

Surprisingly, the inclusion of an aluminum compound potentiates the action of the glycol/cellulose combination so that accelerated wound-healing response is achieved. and further reduces the number of skin grafts that would otherwise have been necessary in the case of treatment of for example burns. Also it is more effective in inhibiting or preventing the formation of hypertrophic scar tissue so that most patients retain full (normal) muscle movement after healing. The coating allows for normal growth of facial hair in the male and on completion of re-epithelisation the coating lifts off spontaneously.

Preferred compositions according to the invention are colourless and may be applied liberally to a patient without staining of clothes.

The composition can be heat sterilized by autoclaving and is believed to exert an inherent bacteriostatic action and to have a degree of activity against a range of viruses or mycellia. It is effective as the sole agent in the treatment of clean superficial burns, cuts, wounds, abrasions and the like.

An advantage of compositions according to the invention is their ability to accept a wide range of agents which can be added for treatment of contaminated or infected wounds in accordance with sensitivity patterns revealed by bacterial culture for the individual patient.

For preference the composition includes one or more antibiotics, antiseptics, corticosteroids or other active agents, or combinations thereof, depending the conditions and nature of the wound to be treated. Any number of such agents are known and can be easily selected by those skilled in the art by reference to standard texts and manuals such as for example British Pharmacopeia 2000 (London), incorporated herein by reference.

The jelly greatly augments penetration of non-vital tissue such as burn eschar and granulations by antibiotics and other agents and in the case of burns allows the effective destruction of pathogenic flora from burned areas by carrying the active agent to the depths of the burn. Release of the active agent is thought to be controlled by the physical nature of the composition.

The term "wound" or "wounds" as used in the context of the present invention is intended to encompass any surface injury which may include burns, abrasions, cuts and other types of wounds. The wound or wounds may be localised on the outer or on the inner surfaces of the body but for preference the wounds to be treated are skin wounds.

DESCRIPTION OF PREFERRED EMBODIMENTS

Figure 1:
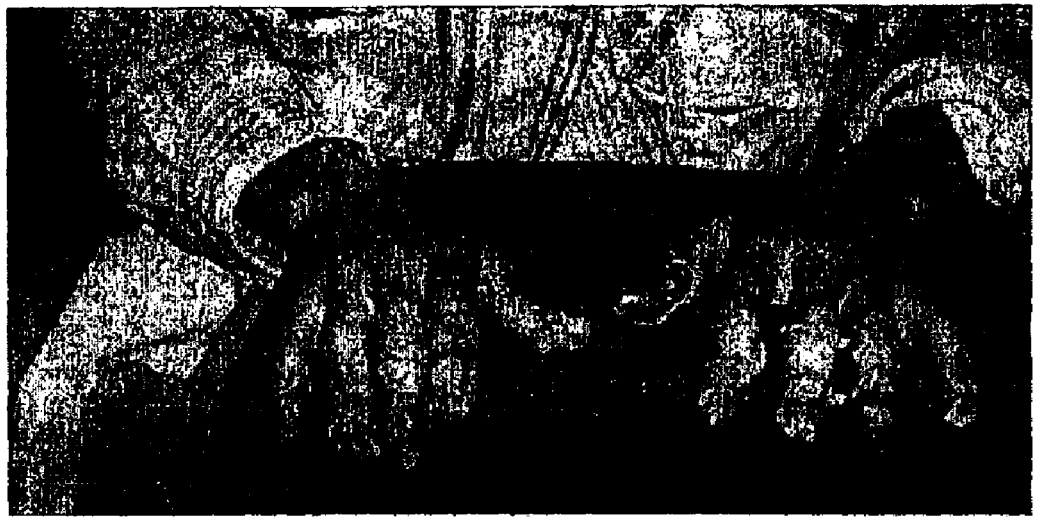
FIG. 1 shows lesions on presentation of a patient suffering deep thermal burns with ill-defined areas of full thickness loss to the circumferential skin of the fingers and thumbs of both hands.

The various embodiments of the invention will now be more particularly described by way of example only.

The composition containing a glycol and a cellulose derivative is described in Australian patent No. 558482, incorporated in its entirety herein by reference, and will be referred to herein as SOLUGEL. Certain embodiments of the present invention make use of SOLUGEL as a base composition for the preparation of the improved is compositions by adding an aluminium containing compound.

A preferred composition in accordance with the present invention is typically as follows (referred to herein as COMPOSITION X):

|  | Percentages w/w |
| --- | --- |
| AR grade Propylene glycol | 25.0% |
| Hydroxy ethyl cellulose | 2.0% |
| Sodium chloride | 0.9% |
| Aluminium acetate | 2% |
| Distilled water | 70.1% |
|  | 100.0% |

A portion of the water used in the examplified formulation may be replaced with one or more other pharmaceutically acceptable carriers or excipients, such as those described in "Remington: The Science and Practice of Pharmacy" 1995 (Mack Publishing Company, Easton Pa.), incorporated herein by reference.

Propylene glycol is preferred as the glycol component of the composition. However it is believed that other pharmaceutically acceptable glycols having more than three carbon atoms could be substituted for propylene glycol. Such alternative glycols and the like agents may be easily identified from standard formulation texts such as "Remington: The Science and Practice of Pharmacy" 1995 (Mack Publishing Company, Easton Pa.), incorporated herein by reference.

If the amount of propylene glycol present exceeds 30% w/v of the compound there is a tendency for the composition to sting some patients. As the proportion of propylene glycol is reduced to below 30% w/v the propensity to cause stinging is reduced. At 25.0% propylene glycol the incidence of reported stinging was acceptably low. At concentrations of propylene glycol below 15% w/v a deterioration in effectiveness is noticed and therefore concentrations greater than 15% and desirably greater than 20% are preferred. The range from 22.5–27.5% w/v is still more highly preferred.

The hydroxyethyl cellulose is importantly a heat sterilizable substance, when such property is advantageous, which forms a gel with water and the amount required is chosen having regard to the desired consistency of the gel. From 0.5 to 4% w/v is a preferred range and more preferably from 1% to 3% w/v. Other gel-forming heat sterilizable celluloses may be used and such agents may be easily identified from standard formulation texts such as "Remington: The Science and Practice of Pharmacy" 1995 (Mack Publishing Company, Easton Pa.), incorporated herein by reference. Hydroxyethyl cellulose available from A. C. Hatrick under the name Natrosol* (*Natrosol is a registered trade mark) was found to more readily form a gel of suitable and smooth consistency with the propylene glycol in contrast to hydroxymethyl cellulose and was found to retain a satisfactory gel structure after sterilization by autoclaving.

The preferred aluminium containing compound is aluminium acetate which may be present in the composition typically from about 0.5 to about 10% w/v and preferably it is present at about 2% w/v.

The inclusion of sodium chloride in the composition is optional and also serves to reduce stinging when the gel is applied on raw areas. The amount of salt present is preferably within the range of 0–2%.

By way of example of a method of preparation of the gel, the formulation hydroxy ethyl cellulose is first dispersed in the formulation propylene glycol. The salt, if any, is dissolved in the formulation water which is heated to approximately 60° C. The hydroxy ethyl cellulose/propylene glycol dispersion is then stirred slowly into the water. Stirring and heating is maintained until thickened. This composition is referred to herein as SOLUGEL. The temperature is then maintained at between approximately 60C to 80C while aluminium acetate powder is added or alternatively a known quantity of prepared SOLUGEL is heated to 60–80° C. and finely divided aluminium acetate powder is slaked into a fine paste using five times its mass of SOLUGEL, the paste thereafter is introduced to the mass of heated SOLUGEL and dispersed by gentle agitation. The mixture is stirred until the aluminium acetate dissolves in the gel. Thus prepared composition of the present invention is then dispensed into sealable heat proof containers and steam autoclaved to produce surgical sterility.

The gel compositions according to the present invention may also contain one or more specific additives such as the following:
1. Antiseptic which may be present typically in an amount from 0.02 to 1.0% w/v of the composition. Suitable examples are chlorhexidine acetate or chlorhexidine gluconate.
2. Antibiotic which may be present in an amount from about 0.1 to about 0.4% w/v of the composition. A suitable example is gentamicin sulphate.
3. Topical corticosteroid which has a variety of functions but in particular is an anti-inflammatory agent, and may be present typically in an amount of up to 1% w/w of the composition and preferably of from 0.4 to 0.6% w/v.

Hydrocortisone added typically in concentrations of 0.5% has been clearly shown to make the jelly dramatically effective in the treatment of sunburn, first degree burns, acute uticatia, insect bites and the like. Symptomatic relief occurs within several minutes and inflammation is typically suppressed within 24 hours.

Compositions according to the invention may be used as the main dressing agent in both major and minor burns and in the management of wounds such as varicose ulcers and bedsores. It is envisaged that such compositions could also be used in dermalogical preparations with the addition of suitable specific additives and for household use in the treatment of minor burns, sunburn, cuts, wounds, abrasions and the like. Further, the compositions of the present invention may be used as an oral preparation for the treatment for example of gingival disease or as a dressing after gingivectomy. Also, the compositions of the present invention may be used in the treatment of for example haemorrhoidectomy wounds and the like.

When applied with tulle gras under gladwrap in closed dressings, the jelly maintains its physical state for up to five days and thus prevents adherance of dressings to raw surfaces and allows dressings to be carried out without gross discomfort and pain, thus minimising the need for dressings under general anaesthetic.

When used in repeated applications to exposed surfaces the jelly dries to a flexible impervious coating, reacts with the surface exudate of the wound and thereafter forms a firm bond which can be soaked off readily if desired, or left insitu to peel off spontaneously when re-epit helisation has occurred. Whilst insitu the coating is a highly effective barrier against bacterial contamination and mechanical abrasion. Crusting and scab formation is prevented and normal hair growth is permitted. (This is particularly pertinent in burns in the beard area of the male face). The jelly is effective in burns of the face and perineam, and in the after care of facial dermabrasion; greatly increasing patient comfort and greatly reducing the chance of bacterial contamination.

Properly administered (see treatment plan below), the jelly has been found to minimise the formation of hypertrophic scar formation in resolved deep dermal burns and in small areas of fall thickness burns healed by secondary intention. It also promotes the formation of dense well vascularised sterile granulating as graft bed, graft take has been improved dramatically and secondary scar hypertrophy and graft contractures across flexor surface has been shown to be greatly reduced.

When applied to fresh wounds exhibiting capillary ooze eg. Graft donor sites and area of fresh dermabrasion, the jelly has been found to produce effective haemostasis within a few minutes, after application under tulle gras and application of pressure, thus eradicating the presence of dried blood clot, a source of discomfort and possible medicine for bacterial propagation.

The compositions of the present invention may be applied to dressings such as for example adhesive strip-type dressings, pads, bandages and the like, and either used immediately for wound dressing or stored for future use. The dressing may be impregnated with the compositions of the invention or they may be simply applied to one surface of the dressing. The dressings can be suitably modified or made by known means and from known materials, to be suitable for use in the oral cavity or the anal canal.

The following case histories further illustrate methods of treatment according to the invention. References to "jelly" in the case histories refer to the improved composition according to the present invention.

EXAMPLES

Case I

This patient accidentally ignited the fingers of both hands when they were soaked in acetone, suffering deep dermal burns with ill-defined areas of full thickness loss to the circumferential skin of the fingers and thumbs of both hands. He was admitted to the hospital and treated with SOLUGEL-filled polythene bags, elevation and mobilizing physiotherapy. FIG. 1 shows lesions on presentation.

Within ten days mobility had been restored to the fingers and the burned areas were sterile. The plan at this stage was to resolve the areas of partial thickness loss and then to put tailored grafts on the area of full thickness.

Unfortunately the patient absconded from the hospital and went missing for several weeks, during which stage the unresolved areas became heavily infected with mixed bacterial organisms which produced apparent widespread areas of full thickness skin loss and exuberant purulent granulations. After forty eight hours intensive cleansing and dressing with SOLUGEL, the patient was taken to theatre with the aim of shaving the exuberant granulations and at a later stage returning the patient to theatre for skin grafting.

Figure 2:
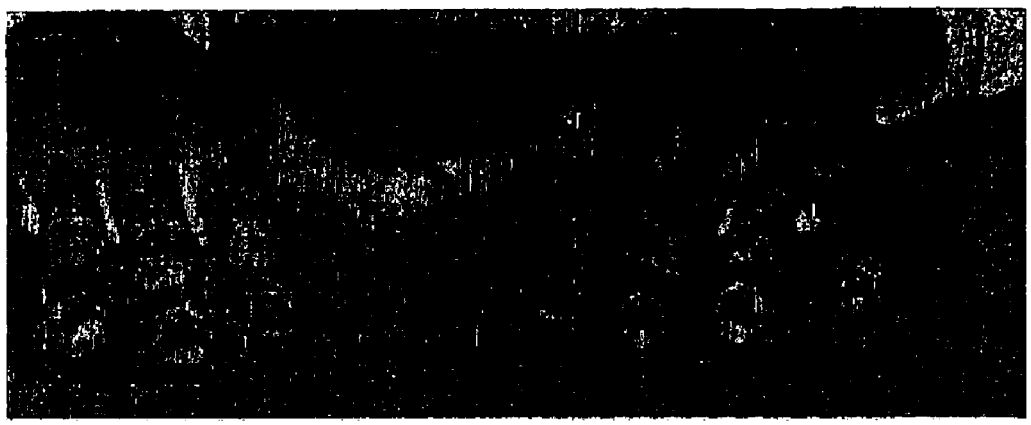
FIG. 2 shows rapid and complete recovery of wounds after application of COMPOSITION X.
Figure 3:
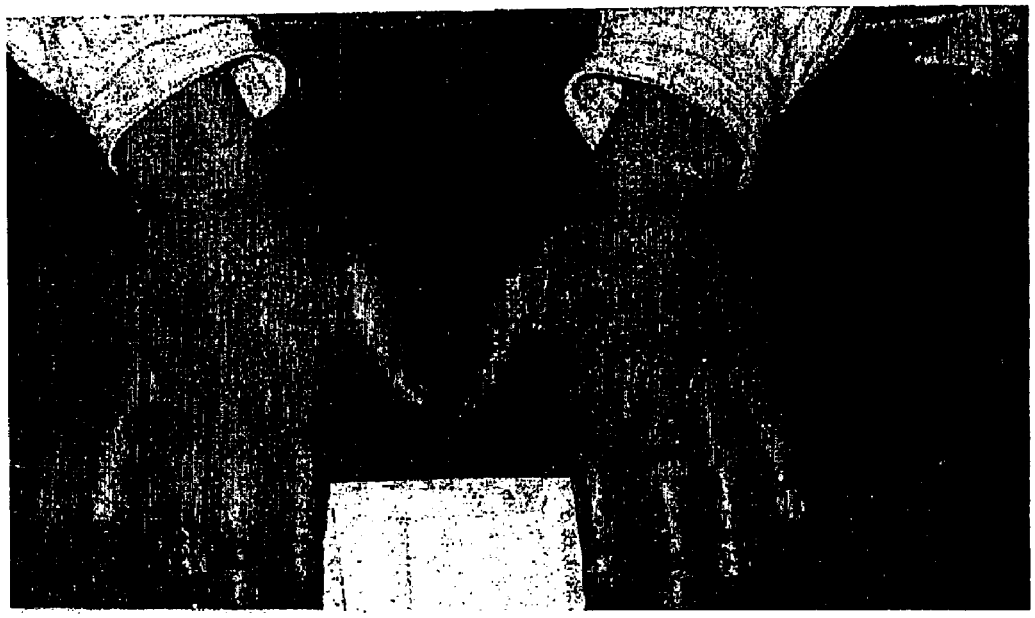
FIG. 3 shows the hands to be completely healed within a six week treatment period.

After granulation shaving the patient volunteered to have treatment with an improved composition of the present invention, COMPOSITION X. Completely without precedent and totally unexpectedly when COMPOSITION X was applied to the wounds they resolved rapidly and completely (FIG. 2). Within a six week treatment period hands completely healed without any residual scarring and with normal function (FIG. 3).

Figure 4:
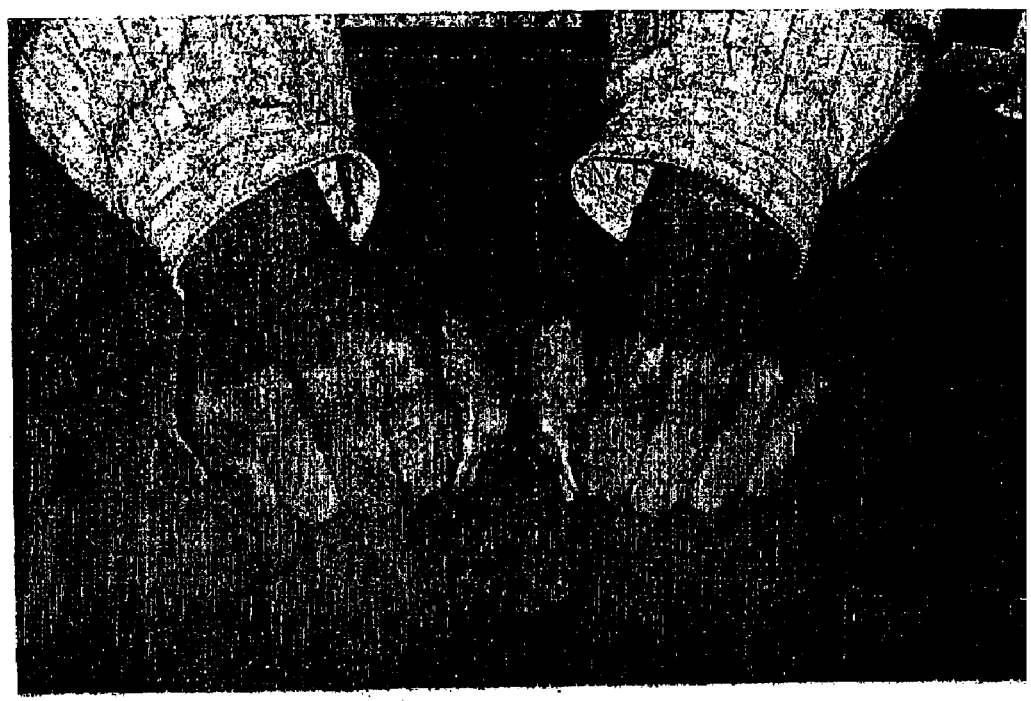
FIG. 4 shows no late development of post-burn scarring two years after the original injury.

The unique aspect of this case is that even in ares of apparent full thickness skin loss the patient's normal fingerprints re-appeared undistorted. Two years after the original injury there was no late development of post-burn scarring, and the fingernails and paronychial folds regenerated with no residual scarring or deformity (FIG. 4).

Case II

A fifty eight (58 year) old man presented with a squamous cell carcinoma on the skin on the right side on the bridge of his nose. His skin was severely sun damaged with a large number of cutaneous malignancies and pre-malignancies in all the areas that might have been used for matching flap or skin graft to close the deficiency.

Figure 5:
FIG. 5 shows an area immediately after excision of malignancy from a man presenting a squamous cell carcinoma on the right side on the bridge of his nose.
Figure 6:
FIG. 6 shows shrinking and resolution progressing 18 days after excision of the malignancy and initiation of treatment with COMPOSITION X.
Figure 7:
FIG. 7 shows resolution without hypertrophic scarring and without any deformity of the eyelids, cheek lines or nostril margins 48 days after initiation of treatment with COMPOSITION X.

Therefore with his consent a conservative closure using COMPOSITION X was selected as the means of repair. FIG. 5 shows the area immediately after excision of the malignancy. FIG. 6 shows shrinking and resolution progressing 18 days after excision of the malignancy and the initiation of treatment with COMPOSITION X. Of note is the total lack of inflammation or infection, regardless of the fact that antibiotics were not used in this case. FIG. 7 shows that 48 days after initiation of treatment with COMPOSITION X the resolution has occurred without hypertrophic scarring and without any deformity of the eyelids, cheek lines or nostril margins.

Case III

Another example of conservative closure of post-surgical zone of full thickness loss using patient home administered dressing covered with COMPOSITION X. The patient remained normally ambulant and pain free during the resolution period and the surgery itself required only an office procedure.

Figure 8:
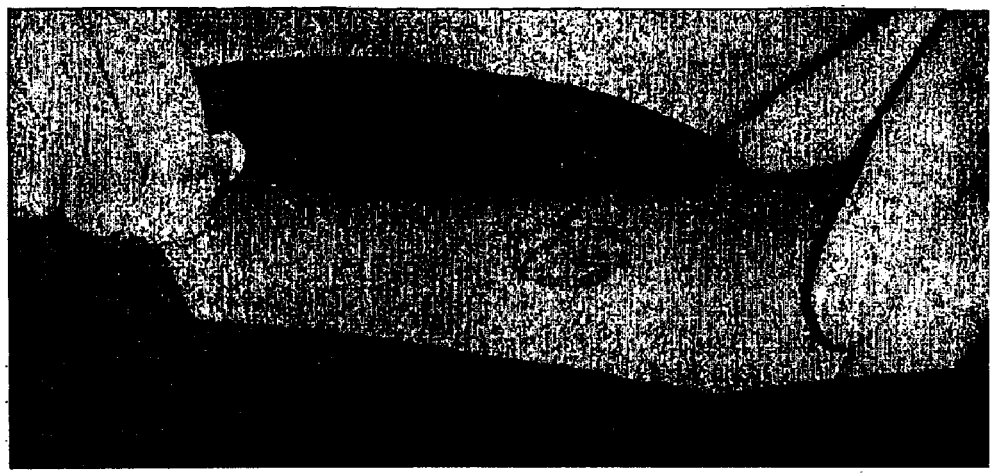
FIG. 8 shows an area that was widely excised, leaving an area of full thickness skin loss floored with subcutaneous fat.

The patient presented with an extensive area of intra-epithelial squamous cell carcinoma on the skin of the right medial calf. She had an intercurrent diagnosis of moderately severe perforating varicose veins and moderated oedema of the lower calves and ankles was noted on presentation. The area was widely excised leaving an area of full thickness skin loss floored with subcutaneous fat (FIG. 8).

Figure 9:
FIG. 9 shows healing that appears to have stalled by about 10 weeks of treatment with SOLUGEL.

At the time of the procedure a regime of SOLUGEL dressings was introduced. Possibly on account of the patients intercurrent problem with varicose veins and oedema, the rate of resolution was slow and by about 10 weeks the area was swollen and itchy and healing appeared to have stalled (FIG. 9). With the patients permission therefore dressings with COMPOSITION X were substituted for SOLUGEL. It was noted that the swelling and itchiness subsided within two (2) days and the spontaneous healing was vigorously re-activated.

Figure 10:
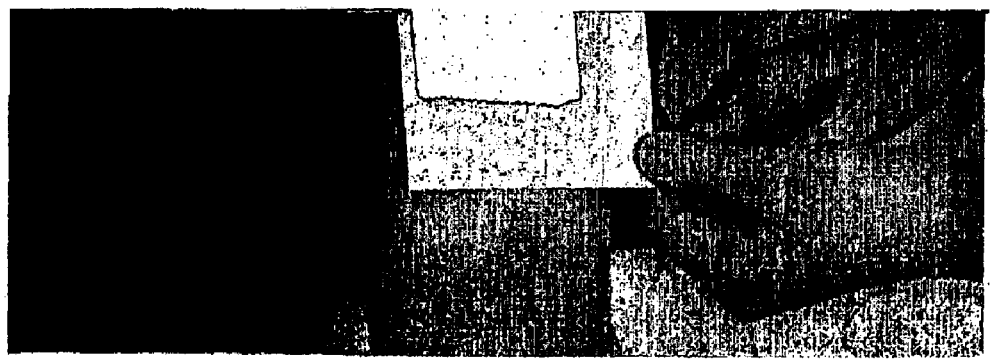
FIG. 10 shows wound healing at 6 weeks from initiation of treatment with COMPOSITION X.

Resolution was thereafter rapid and asymptomatic and wound healing had been confirmed at six weeks from initiation of treatment with COMPOSITION X (FIG. 10). The area of full thickness skin loss was covered with a much smaller area of skin of normal consistency and colour lacking only hair follicles.

Case IV

A sixty (60) year old metal worker presented with a full thickness burn on the lateral surface of his left heel and instep, caused by molten zinc that penetrated his protective boots.

Figure 11:
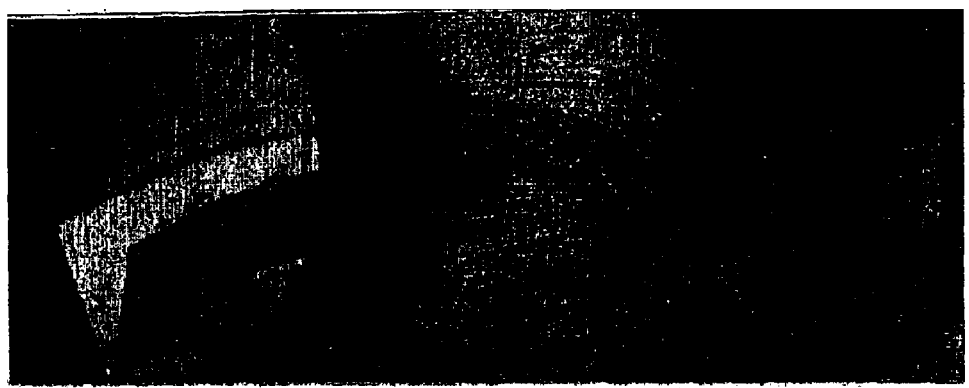
FIG. 11 shows the result of treatment with SOLUGEL, where the wound did not re-epithelize in the areas of deep full thickness skin loss.

This patient had suffered a less severe metal burn on the lateral surface of the left calf two years earlier, which had been successfully treated with SOLUGEL and Sofra Tulle. So instead of returning to my care after the present incident, he was treated elsewhere with SOLUGEL. The result of this treatment was that although the wound cleaned and decreased somewhat in width it did not re-epithelize in the areas of deep full thickness skin loss and the patient was referred to me (FIG. 11)

With the patients permission the treatment was modified by introducing COMPOSITION X.

Figure 12:
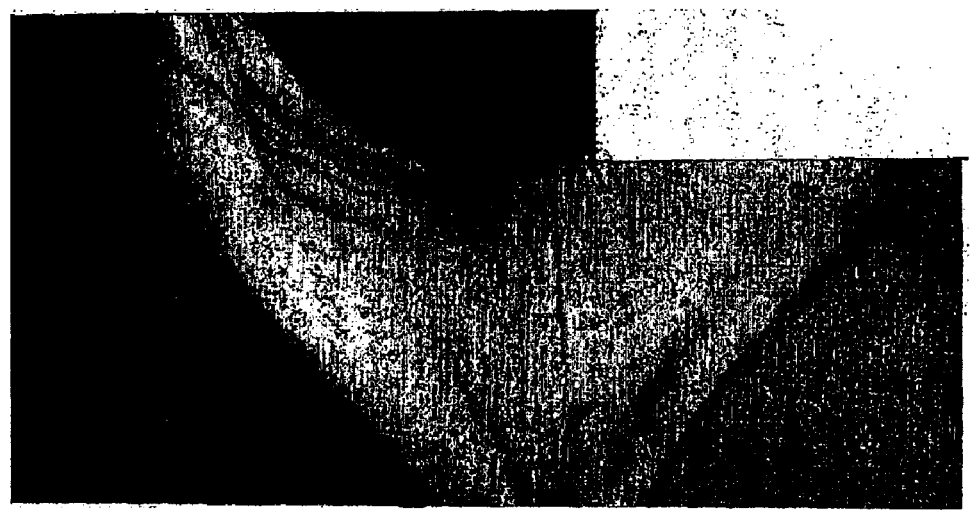
FIG. 12 shows epithelization of the total area by two weeks of treatment with COMPOSITION X.
Figure 13:
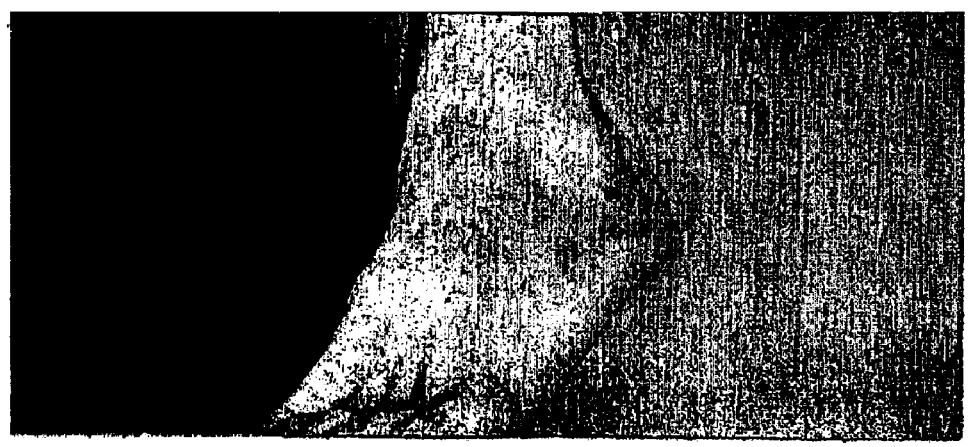
FIG. 13 shows the involved wound area resolved to virtually normal skin.

Epithelization of the total area was seen to be advanced by two weeks of treatment (FIG. 12) and by 3 weeks epithelization was advanced in all areas but in the posterior zone on the lateral surface of the heel. The dressing technique was modified to give a better distribution of COMPOSITION X to this area and epithelization was complete two weeks later. The involved wound area resolved to virtually normal skin with an absolute minimum of scarring (FIG. 13), the scarring being confined to the lateral surface of the heel.

It was noted that even though the anterior segment of the scar was over the dorsi-flexor line of the instep of the foot, that no flexor contractures occurred.

When this patient was recently re-examined, the area of deep burn on the lateral side of the foot had resolved to the point where it was completely undetectable, normal skin with apparent, normal mobile subcutaneous tissue was present in the entire area including the slowly healing area on the lateral surface at the posterior end of the zone. It was noted interestingly that there was a normal passage of subcutaneous veins through the area continuous with the subcutaneous veins above and below the area. Higher on the lateral surface of the same leg, in the area treated several years earlier with SOLUGEL, it was noted that although the wound remained firmly healed that there was definitive scarring that adhered to the deep fascia in the area.

Case V

A fifty six (56) year old male with a history of multiple cutaneous basal cell carcinomas and squamous cell carcinomas who had had multiple excisions in my hands over the period of a decade. He had previously been the subject of a conservative SOLUGEL closure of post-operative deficiencies on the arms and legs and when it was necessary to widely excise a squamous cell carcinoma from the skin adjacent to the thenar web of his right hand, he consented to a trial of conservative closure using COMPOSITION X. The particular area concerned here presented special difficulties because of the high degree of mobility and stretching of the skin inseparable from the normal functional movements of the fingers and hand.

Figure 14:
FIG. 14 shows surgery to excise a squamous cell carcinoma.
Figure 15:
FIG. 15 the surgery site by day 6.
Figure 16:
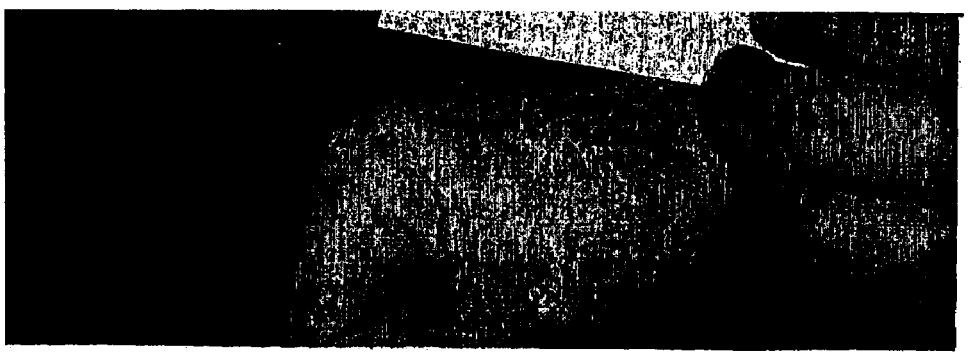
FIG. 16 shows complete resolution of the area with minimal linear hypertrophic scar by 10 weeks of treatment with COMPOSITION X.

The surgery was carried (FIG. 14) and it will be noted that by day 6 (FIG. 15) the prevailing cutaneous stresses in the area had widened the skin deficiency created by the surgery by about 30%. The patient performed his own dressings with COMPOSITION X and by 10 weeks of treatment with COMPOSITION X complete resolution of the area was evident with a minimal linear hypertrophic scar (FIG. 16) which has since resolved. More importantly, the position of the hand shows that full function has been maintained with total scar stability.

One of the advantages provided by the compositions of the present invention is that wounds treated with the compositions resolve significantly faster and with a significantly greater depression of scarring when compared to the SOLUGEL composition.

It has been repeatedly demonstrated that areas of extensive undoubted full thickness skin loss have resolved rapidly to a situation where instead of expected hypertrophic scarring, the areas concerned have been re-surfaced with skin of normal texture and flexibility, regardless of the fact that in several cases the full thickness skin deficiency lay across flexor creases where contracted hypertrophic scars would be the inevitable result of conservative healing of full thickness skin loss in such areas. Further, in areas of full thickness skin loss extending to underlying structures, such as muscle and tendon, the resolved skin cover after healing has been found to be non-adherent to underlying structures, indicating that at least some resolution of subcutaneous soft tissue has occurred.

In addition it has been noted that immediate post-operative dressing of surgical wounds with the improved compositions of the present invention induces a remarkably rapid and complication-free resolution; with the early establishment of fine quality hairline scars in which the phase of pink scar hypertrophy is either absent or significantly reduced.

Modifications to and variations of both the composition and methods of treatment hereof such as would be apparent to those skilled in the art are deemed to be within the scope of the disclosure.

What is claimed is:

1. Method for topical treatment of full thickness skin loss including the step of topical application thereto of a composition comprising, per 100 parts by weight, from 15 to 30 parts by weight of a glycol; from 1 to 4 parts by weight of a cellulose derivative; and from 0.5 to 10 parts by weight of a water soluble aluminum salt.

2. Method according to claim 1, wherein the skin loss is a burn.

3. Method according to claim 1, wherein the skin loss is an abrasion.

4. Method according to claim 1, wherein the skin loss is a cut.

5. Method according to claim 1, wherein the skin loss is a post-operative surgical wound.

6. Method according to claim 1, wherein the skin loss is located in the oral cavity or the anal canal.

* * * * *